United States Patent [19]
Davis et al.

[11] Patent Number: 6,027,480
[45] Date of Patent: *Feb. 22, 2000

[54] CATHETER INTRODUCER

[75] Inventors: Bryan G. Davis; Mark A. Crawford; Glade H. Howell, all of Sandy, Utah

[73] Assignee: Becton Dickinson and Company, Franklin, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/909,223

[22] Filed: Aug. 11, 1997

[51] Int. Cl.[7] ................................. A61M 5/178
[52] U.S. Cl. .............................. 604/164; 604/177
[58] Field of Search .................... 604/164, 160, 604/165, 177, 174

[56] References Cited

U.S. PATENT DOCUMENTS

| | | | |
|---|---|---|---|
| 3,677,243 | 7/1972 | Nerz | 128/214.4 |
| 4,166,469 | 9/1979 | Littleford | 128/784 |
| 4,243,050 | 1/1981 | Littleford | 128/784 |
| 4,306,562 | 12/1981 | Osborne | 128/348 |
| 4,345,596 | 8/1982 | Young | 128/214 R |
| 4,449,973 | 5/1984 | Luther | 604/161 |
| 4,451,256 | 5/1984 | Weikl et al. | 604/164 |
| 4,581,019 | 4/1986 | Curelaru et al. | 604/164 |
| 4,596,559 | 6/1986 | Fleischhacker | 604/170 |
| 4,772,266 | 9/1988 | Groshong | 604/164 |
| 4,865,593 | 9/1989 | Ogawa et al. | 604/264 |
| 4,954,130 | 9/1990 | Edwards | 604/169 |
| 5,098,392 | 3/1992 | Fleischhacker et al. | 604/165 |
| 5,125,904 | 6/1992 | Lee | 604/164 |
| 5,141,497 | 8/1992 | Erskine | 604/165 |
| 5,167,634 | 12/1992 | Corrigan, Jr. et al. | 604/160 |
| 5,221,263 | 6/1993 | Sinko et al. | 604/161 |
| 5,250,033 | 10/1993 | Evans et al. | 604/160 |
| 5,318,542 | 6/1994 | Hirsch et al. | 604/161 |
| 5,334,157 | 8/1994 | Klein et al. | 604/160 |
| 5,354,281 | 10/1994 | Chen | 604/177 |
| 5,397,311 | 3/1995 | Walker et al. | 604/160 |
| 5,536,255 | 7/1996 | Moss | 604/161 |

FOREIGN PATENT DOCUMENTS

| | | | |
|---|---|---|---|
| 0139091 | 5/1985 | European Pat. Off. | A61M 5/14 |
| 2104226 | 12/1971 | Germany | A61M 5/14 |
| 1381053 | 1/1975 | United Kingdom | A61M 25/00 |

*Primary Examiner*—Wynn Wood Coggins
*Assistant Examiner*—N. Kent Gring
*Attorney, Agent, or Firm*—Eric M. Lee

[57] ABSTRACT

A catheter introducer is disclosed having a splittable introducer and an introducer needle. The splittable introducer includes a pair of wings and a tray with an open top extending from the proximal end of the introducer cannula between the wings to lead the distal end of a long, thin and flexible medical device into the open proximal end of the splittable introducer cannula.

22 Claims, 10 Drawing Sheets

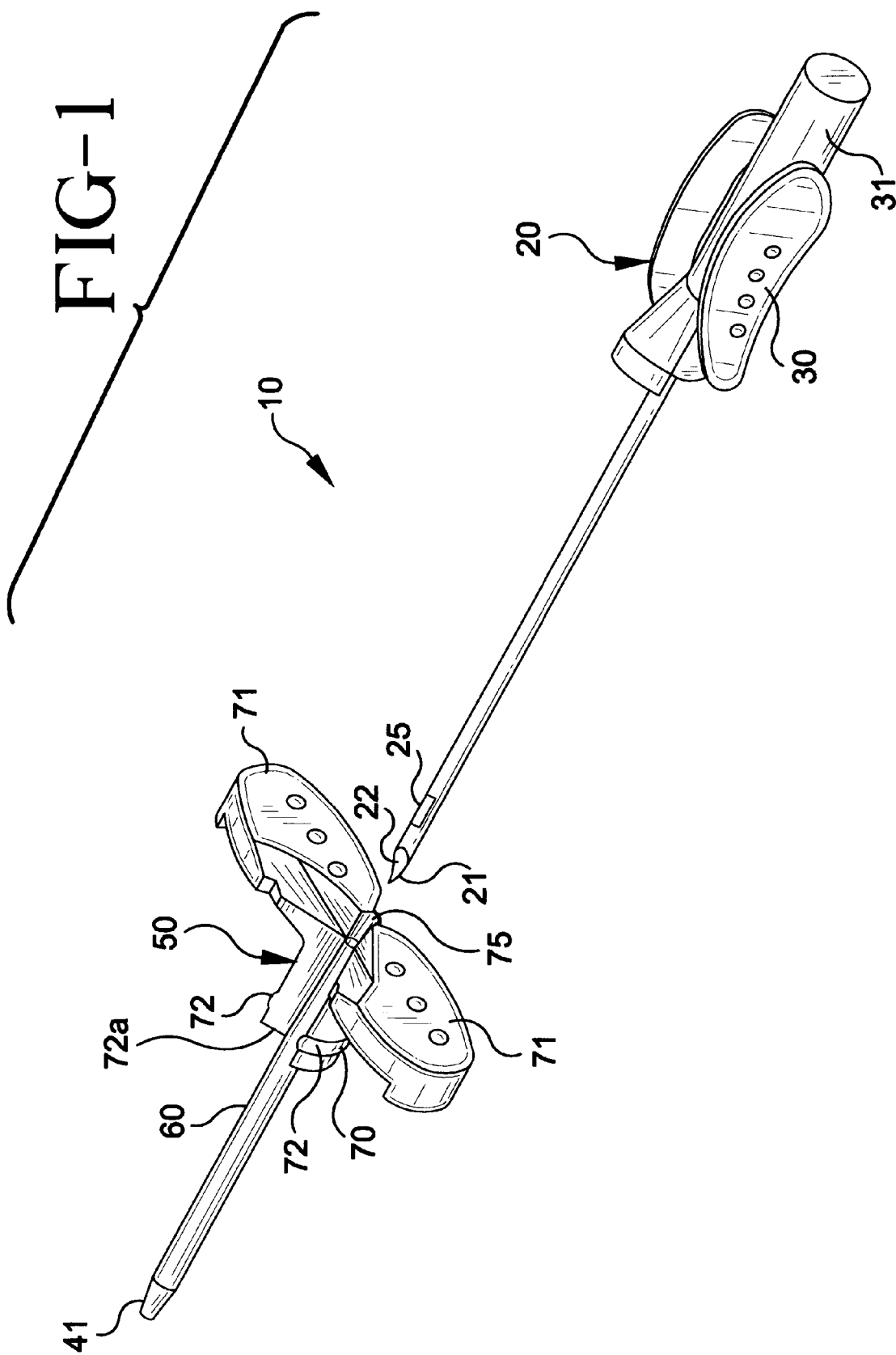

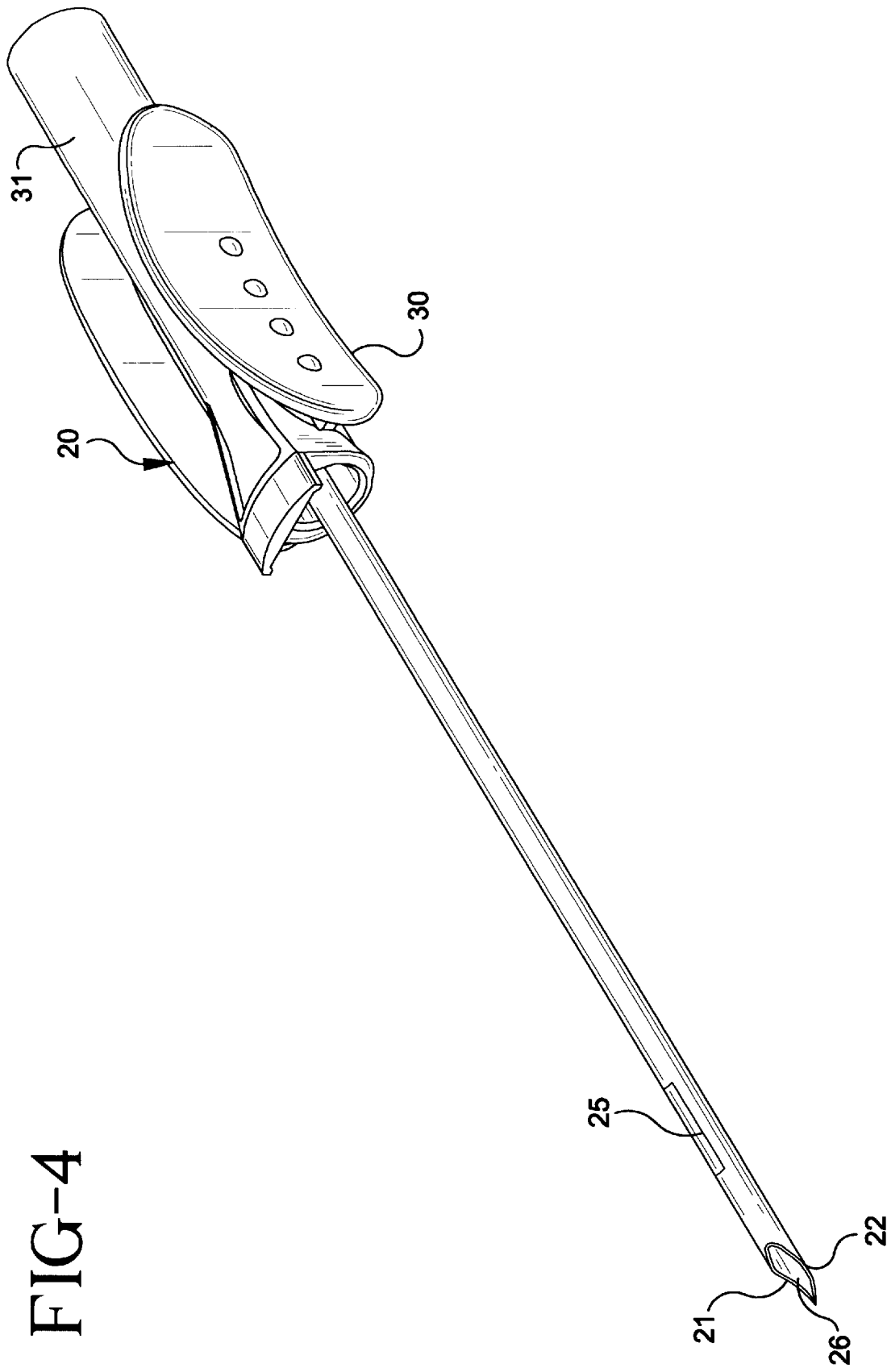

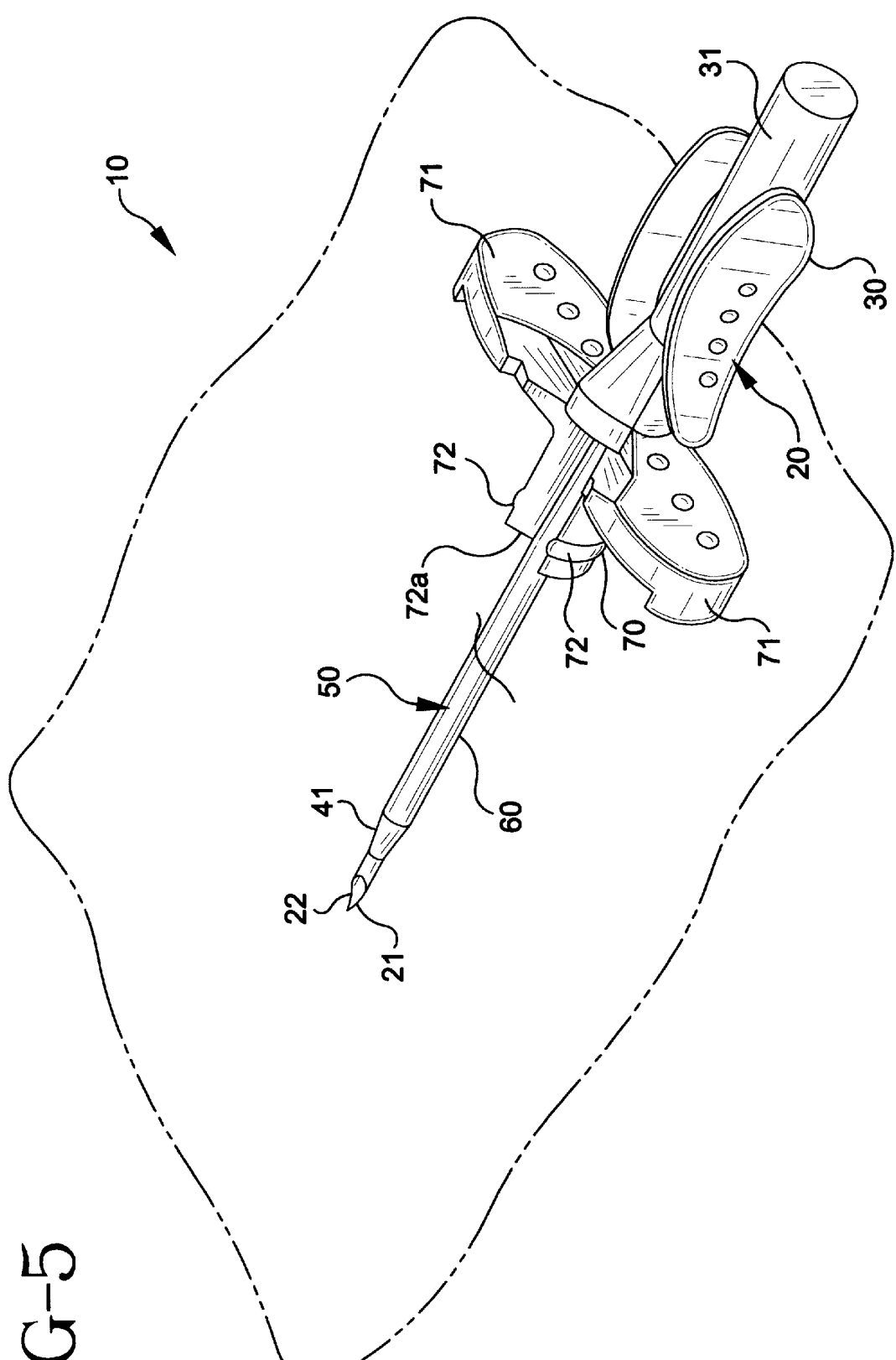

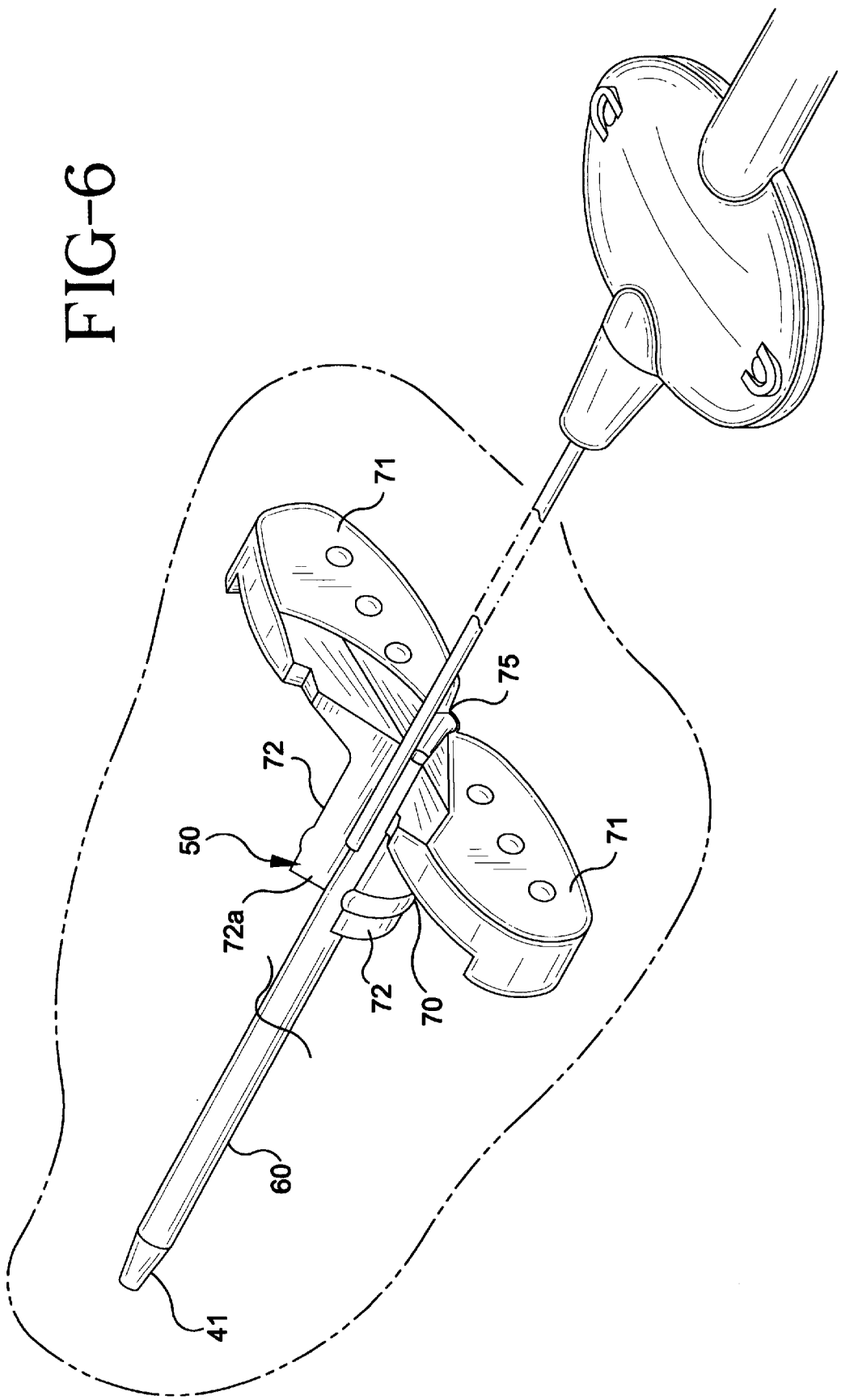

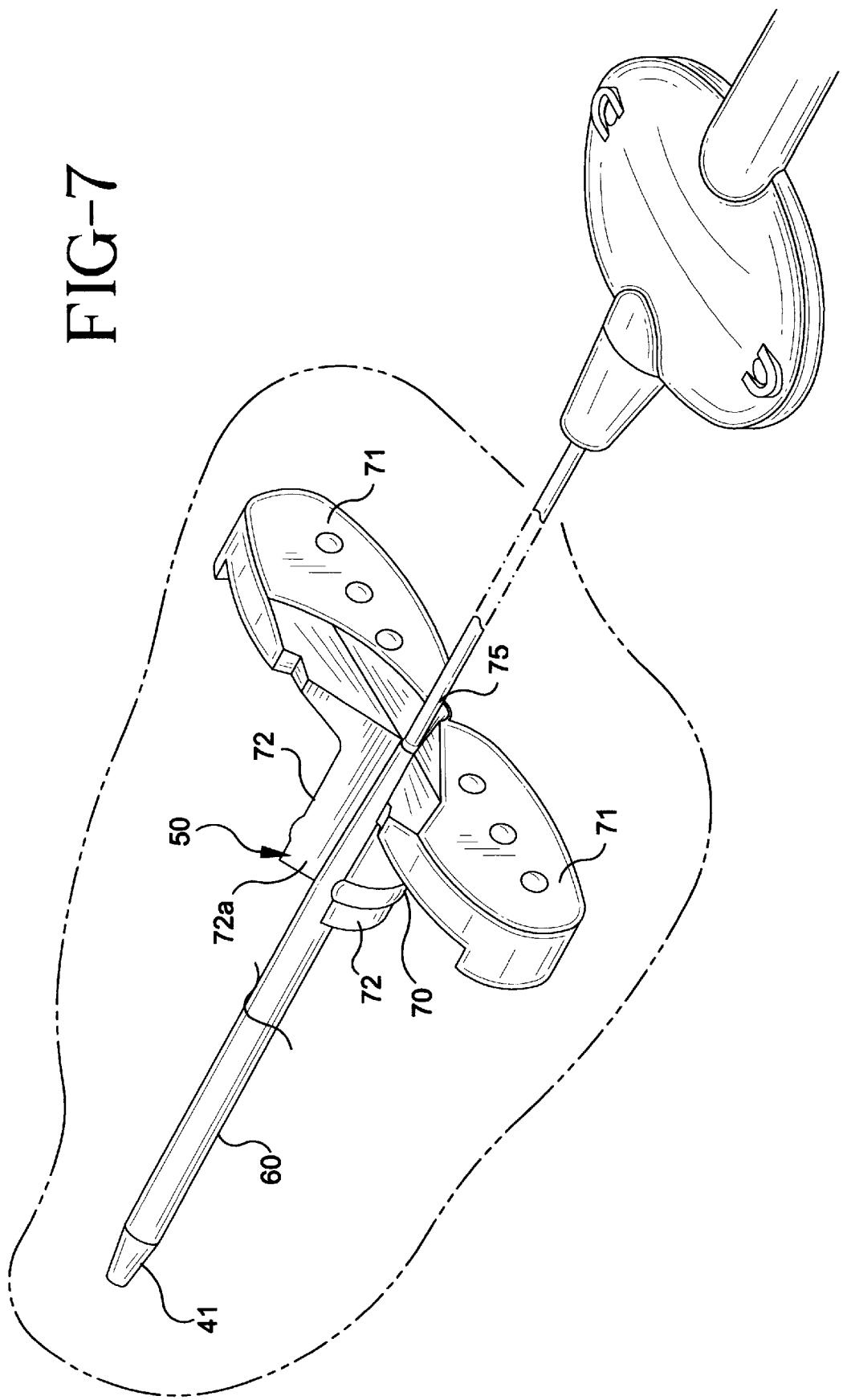

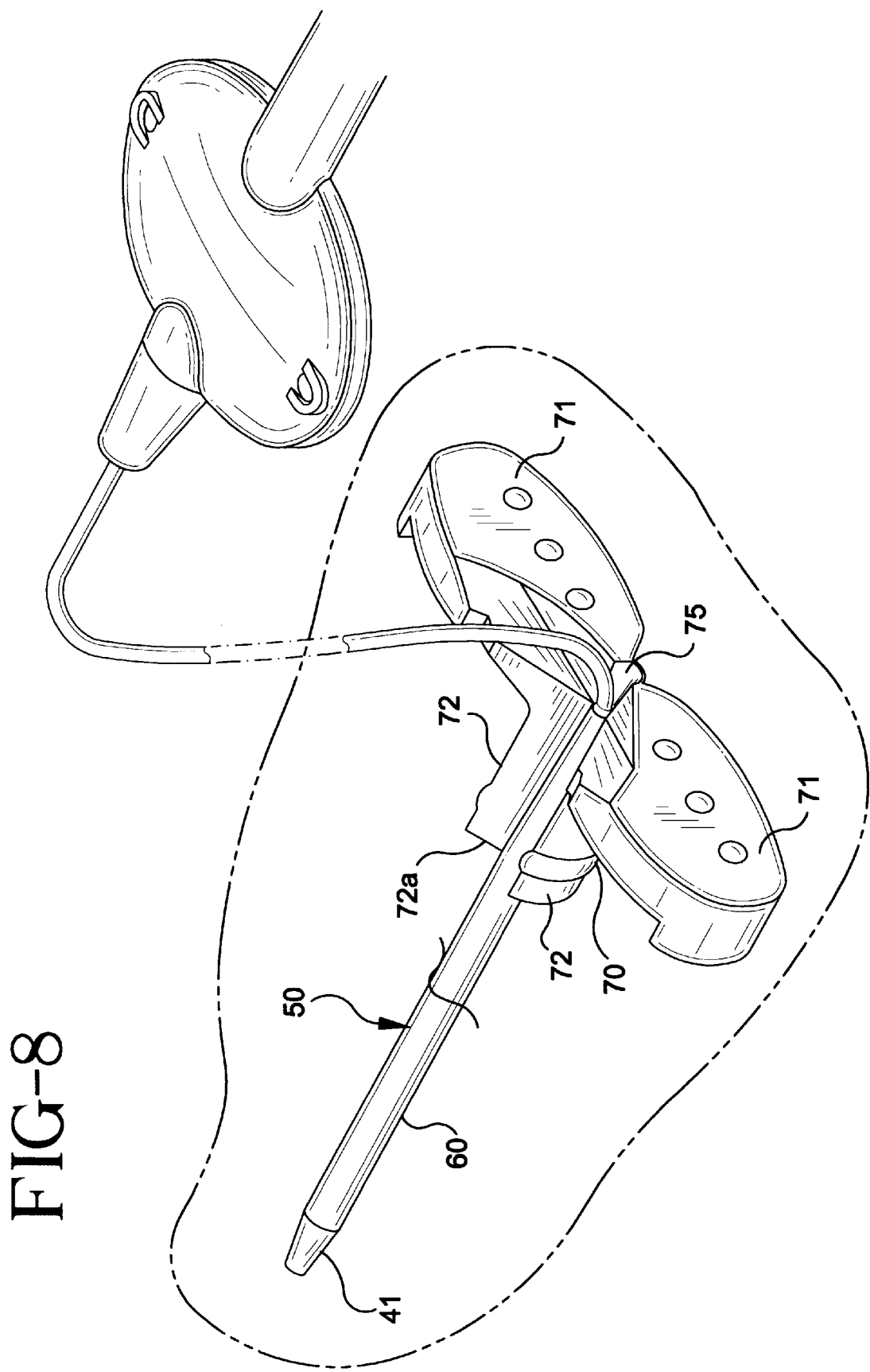

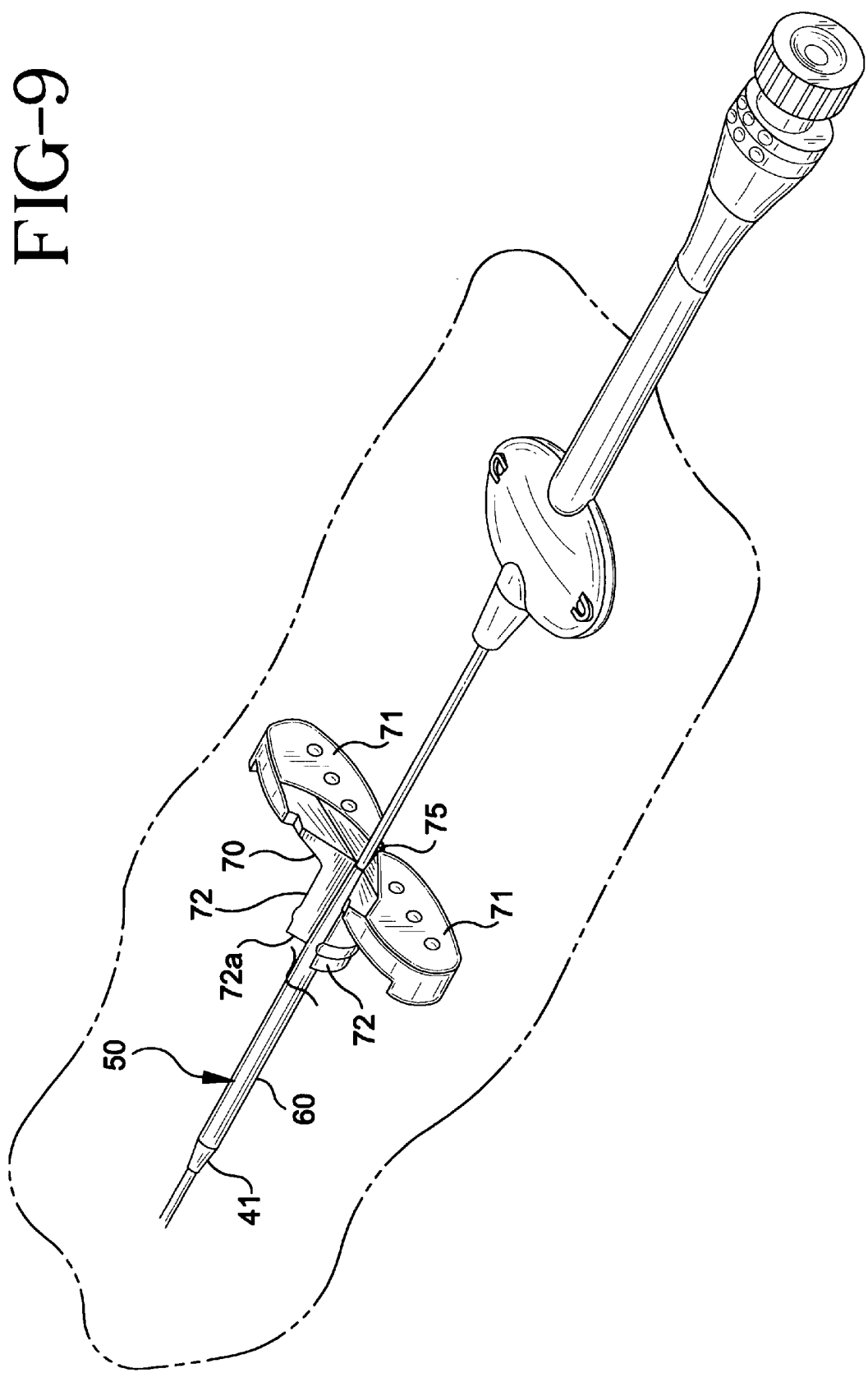

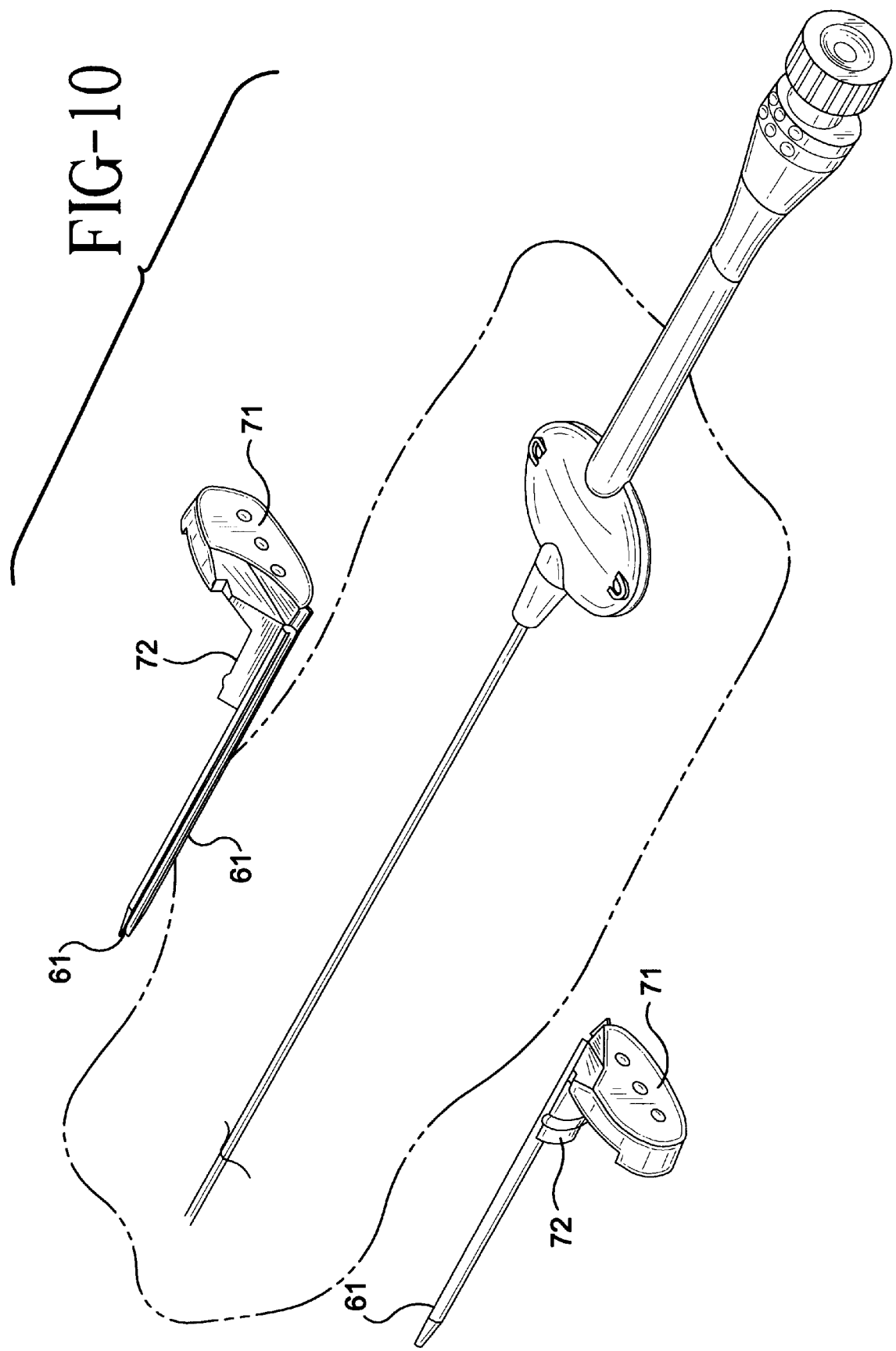

CATHETER INTRODUCER

BACKGROUND OF THE INVENTION

This invention relates to a device for introducing a long, thin and flexible medical device, such as a catheter, into a patient's vasculature. More particularly, this invention relates to an improved catheter introducer that facilitates insertion of the catheter introducer into a patient's vasculature and that allows easy insertion of a catheter through the catheter introducer and into the patient's vasculature.

Catheter introducers are typically used in conjunction with peripherally inserted central catheters (PICC), or other relatively long, thin and flexible medical devices, to facilitate insertion and placement of the catheter or other medical device into the patient's vasculature. Current catheter introducers include a splittable cannula and a hub with a pair of wings fixed to the proximal end of the cannula. In addition, such a catheter introducer includes an introducer needle that is disposed in the splittable cannula with the sharp distal tip of the needle extending distally of the distal end of the splittable cannula and with the needle hub extending proximal of the wings and hub on the cannula. As used herein, the term "proximal" refers to a location on the device closest to the clinician using the device. Conversely, the term "distal" refers to a location on the device farthest from the clinician and closest to the patient into whom the device is to be inserted.

When using a typical catheter introducer, the clinician grasps the needle hub so the needle bevel is facing away from the patient's skin and proceeds to insert the distal portion of the needle and cannula at the desired site in the patient's skin. The clinician continues to advance the device until venipuncture has been confirmed. This confirmation is usually done visually when the clinician sees blood entering a flashback chamber formed in the needle hub at the proximal end of the needle. After venipuncture has been confirmed, the clinician advances the cannula distally into the patient's vein and the needle is withdrawn. With the catheter introducer properly placed, the clinician can then insert the PICC, or other relatively long, thin and flexible medical device, into the proximal opening of the cannula and continue to advance the catheter through the catheter introducer until the catheter is properly placed in the patient's vasculature. Alternatively, the introducer needle can be first placed into the patient's vasculature without the catheter introducer. A guidewire is then inserted through the introducer needle into the patient's vasculature. The introducer needle is then removed leaving the guidewire in place to provide a track or guide for the catheter introducer, and dilator if used, to follow into the patient's vasculature. A catheter is then inserted into the catheter introducer over the guidewire. This greatly facilitates the placement of a PICC into a patient's vasculature. After placement of the PICC, the clinician grasps the wings and pulls them apart to split the splittable introducer. In this way, the splittable introducer can be removed from the patient over any hub located on the proximal end of the PICC.

Although currently available catheter introducers generally work in accordance with their intended purpose, they could be improved. For example, when the catheter introducer is inserted into the patient, the hub is adjacent to the patient's skin and blood flows out of the open proximal end of the splittable cannula. This makes it difficult for the clinician to line up the distal end of the catheter with the open proximal end of the splittable cannula. This is especially problematic since the clinician must always approach the open proximal end of the splittable cannula with the distal end of the catheter along the longitudinal axis of the splittable cannula and since the outer diameter of the catheter is only slightly smaller than the inner diameter of the splittable cannula. In addition, the location and configuration of the wings on the splittable cannula require a certain minimum insertion angle for the device that in some cases may be too large.

SUMMARY OF THE INVENTION

It is therefore an object of the invention to provide a catheter introducer that facilitates aligning the distal end of a catheter or other long, thin and flexible medical device with the open proximal end of the cannula.

It is another object of the invention to provide a catheter introducer that allows the clinician to approach the open proximal end of the splittable cannula with the distal end of a catheter or other long, thin and flexible medical device along a line other than coincident with the longitudinal axis of the splittable cannula.

It is still a further object of this invention to provide a catheter introducer that allows a clinician to use a low insertion angle during venipuncture.

The catheter introducer of this invention comprises an introducer needle having a needle hub and integrated flashback chamber connected to the proximal end of the introducer needle and a splittable introducer with a hub and a pair of wings connected to the proximal end of the splittable introducer. The introducer needle has a sharp distal end and is initially disposed in the splittable introducer such that the sharp distal end of the introducer needle extends distally of the distal end of the splittable introducer. In addition, in this position the needle hub is proximal of the proximal end of the wings of the splittable introducer.

The bevel at the distal end of the introducer needle is a standard B bevel but a short bevel could also be used. A short bevel minimizes the chances for piercing the back of the vein during venipuncture on certain patients such as pediatric and neonatal patients. Such a complication can cause discomfort to the patient and result in a hematoma in the area of the vein puncture. The introducer needle also includes a notch, or a side hole, located in the introducer needle wall along the distal portion but proximal of the bevel. This notch and its distal location allows blood to flow into the annular space between the introducer needle and the splittable introducer cannula. In this manner, where the splittable introducer cannula is at least translucent, the clinician can immediately observe flashback upon venipuncture rather than having to wait for blood to flow through the entire needle and then into the flashback chamber. This is especially important where the patient has a low blood pressure and low bloodflow such as in certain oncology and neonatal patients. Furthermore, the introducer needle is connected to the needle hub at a location that is below the center of mass of the needle hub. Thus, the bottom of the introducer needle is closely aligned with the bottom of the needle hub. This allows the clinician to approach the venipuncture site at a low insertion angle since there is minimal interference by the bottom of the needle hub. In addition, this configuration still provides enough surface area on the needle hub for grasping by the clinician.

As used herein the terms "above" and "top" refer to a location on the device away from the patient's skin where the device rests during use, while the terms "below" and "bottom" refer to a location on the device adjacent to the patient's skin on which the device rests during use.

The splittable introducer includes a pair of wings connected to the cannula. The cannula is formed such that it will easily tear along the longitudinal axis. One mechanism for ensuring such tearing is to form the cannula from a longitudinal tear material. Alternatively, the cannula could include longitudinally extending preferential tear lines formed by scoring or perforating the cannula. Collectively, the mechanisms used to ensure that the cannula will easily tear along the longitudinal axis are called preferential tear lines. Such preferential tear lines are preferably about 165° apart. These preferential tear lines facilitate splitting of the cannula. Each wing is located along the proximal portion of the cannula between the preferential tear lines. Placement of the wings in this location allows the user to easily split the cannula along the preferential tear lines. Each wing is connected to the proximal end of the cannula along a short shaft between the preferential tear lines. In this way, the wings and shafts are separated along two grooves extending over the two preferential tear lines. A tray in the form of a half cylinder extends from the proximal end of the cannula between the wings and shafts along one of the grooves. This tray, which is the only material that connects the two wings together, provides a mechanism to lead the distal end of a catheter, guidewire or other long, thin and flexible medical device into the open proximal end of the cannula. The wings are located on the cannula such that the center of mass of the wings is above the longitudinal axis of the cannula. As with the introducer needle and needle hub configuration, this allows the clinician to use the device with a lower insertion angle while at the same time providing enough surface area for the clinician to grasp for manipulating the splittable introducer cannula.

BRIEF DESCRIPTION OF THE DRAWINGS

The preferred embodiments are illustrated in the drawings in which like reference numerals refer to like elements and in which:

FIG. 1 is a perspective view of the catheter introducer of this invention showing the splittable introducer and the introducer needle;

FIG. 4 is a perspective view of the introducer needle; and

FIGS. 5–10 are schematic perspective views showing the insertion of a long, thin and flexible medical device, i.e. a PICC, through the proximal end of the splittable introducer of this invention.

DETAILED DESCRIPTION OF THE INVENTION

Figure 2A:
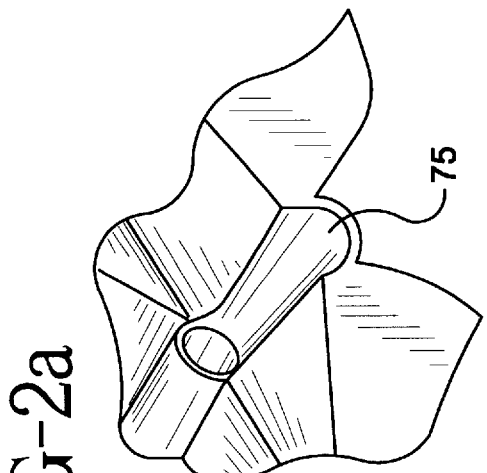
FIG. 2a is an enlarged view of a portion of the proximal end of the splittable introducer showing the tray with an open top.
Figure 2:
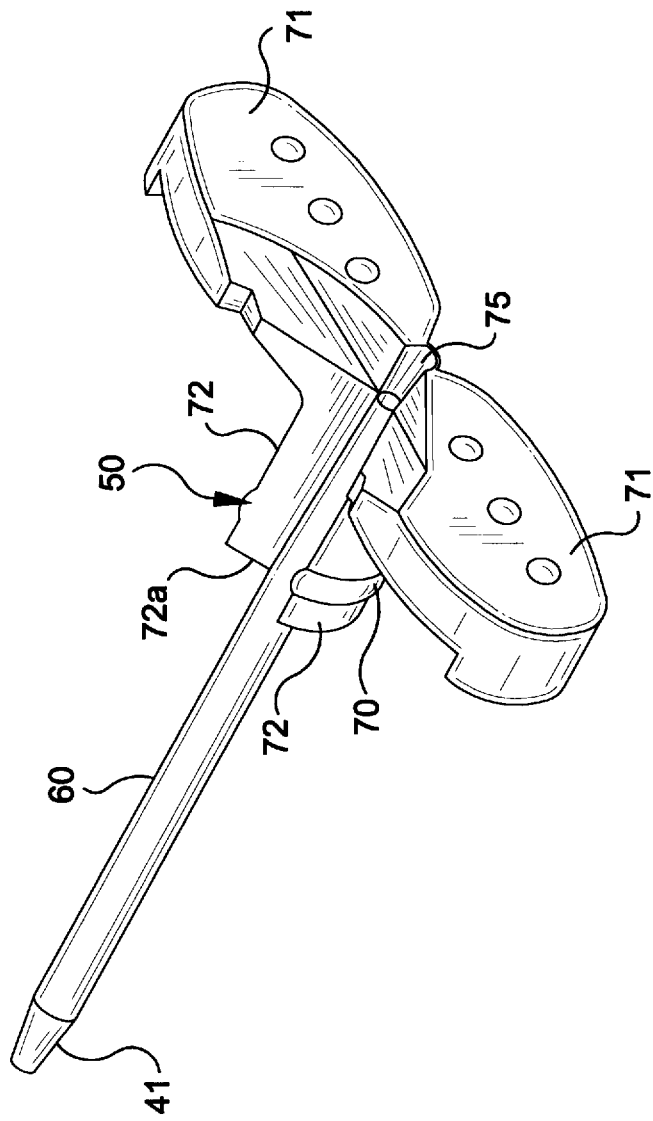
FIG. 2 is a perspective view of the splittable introducer.
Figure 3:
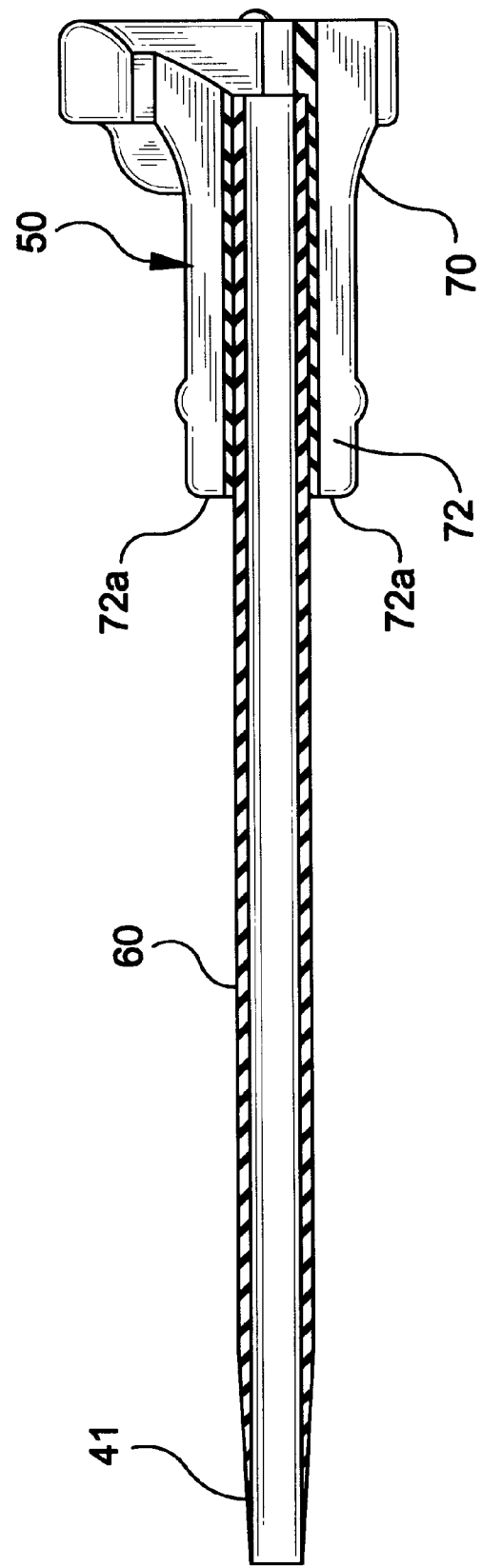
FIG. 3 is a cross-sectional view of the splittable introducer.

The catheter introducer 10 of this invention includes an introducer needle 20 and a splittable introducer 50. See FIG. 1. Typically introducer needle 20 is initially disposed in splittable introducer 50. See FIG. 5. In this configuration, the sharp distal tip 21 of introducer needle 20 extends beyond the distal end 41 of the cannula 60 of splittable introducer 50. In addition, the needle hub 30 of introducer needle 20 is proximal of the hub 70 of splittable introducer 50.

Sharp distal tip 21 of introducer needle 20 is formed by grinding a bevel 22 at the distal end of introducer needle 21. Bevel 22 has a standard B bevel configuration. Alternatively, bevel 22 could be formed having a shorter length than that of a standard B bevel. A shorter bevel length facilitates access to the small veins of certain patients, such as pediatric and neonatal patients, and minimizes the chances that the clinician will pierce the back of the vein during venipuncture Introducer needle 20 also includes a notch, or sideport opening, 25 adjacent to sharp distal tip 21. Notch 25 is in fluid communication with the lumen 26 that extends from the distal end to the proximal end of introducer needle 20. Notch 25 allows blood to flow from inside lumen 26 to the annular space between introducer needle 20 and cannula 60 when catheter introducer 10 of this invention is in the configuration shown in FIG. 5. Thus when the clinician makes a successful venipuncture with catheter introducer 10, blood will be immediately visible to the clinician in that annular space along the distal portion of catheter introducer 10, as long as cannula 60 is at least translucent. Thus the clinician does not have to wait for the blood to travel along the entire length of introducer needle 20 into the flashback chamber 31, which is preferably integral with needle hub 30, located at the proximal end of the introducer needle 20. This immediate indication of successful venipuncture is especially important when the patient has a low blood pressure or low blood flow.

Needle hub 30 is connected to the proximal end of introducer needle 20 so that the longitudinal axis of introducer needle 20 extends below the center of mass of needle hub 30. Offsetting introducer needle 20 and needle hub 30 in this way allows the clinician to approach the venipuncture site at a low insertion angle because of the small distance between the bottom of introducer needle 20 and the bottom of needle hub 30. Thus, needle hub 30 does not engage the patient's skin until the longitudinal axis of introducer needle 20 is substantially parallel to the patient's skin. Preferably, the insertion angle should be less than about 4° at about one inch of useable needle length. Such a low insertion angle minimizes the chances that the clinician will pierce the back of the vein during venipuncture. In addition, since the center of mass of needle hub 30 is located above the longitudinal axis of introducer needle 20, there is a greater surface area on needle hub 30 above introducer needle 20 for the clinician to grasp. This facilitates manipulation of introducer needle 20 by the clinician. Moreover, the bottom of needle hub 30 should not extend significantly below the bottom of the wings 71 of splittable introducer 50. This arrangement ensures that needle hub 30 is not the limiting factor in the insertion angle.

Splittable introducer 50 includes a cannula 60 and a hub 70 connected to the proximal end of cannula 60.

Cannula 60 can be formed from any flexible, biocompatible polymer. However, polyethylene or polytetrafluoroethylene is preferably used. These materials are translucent and allow blood visualization in the annular space between introducer needle 20 and cannula 60. In addition, the material for cannula 60 can be loaded with a certain amount of radiopaque material, such as barium sulfate. The radiopaque material allows a clinician to see cannula 60 under a fluoroscope. This is important if cannula 60 were to somehow break off from hub 70 and enter deep into the patient's vasculature. The radiopacity of cannula 60 allows the clinician to identify its location in the body via a fluoroscope and surgically remove it. Since the radiopaque material renders opaque that portion of cannula 60 loaded with that material, cannula 60 is preferably loaded with stripes of the radiopaque material. This allows at least a significant portion of cannula 60 to remain translucent along its entire length.

Cannula 60 is formed with a pair of longitudinally extending preferential lines 61 which are about 165° apart. Preferential tear lines 61 effectively separate cannula 60 into two pieces. These preferential tear lines 61 allow cannula 60 to be easily split into two pieces when the two portions of cannula 60 are pulled apart by allowing the cannula to be torn along the preferential tear lines 61. Preferential tear lines 61 can be formed by scoring cannula 60 to provide a weakened portion to cannula 60. Alternatively, preferential tear lines 61 could be formed by longitudinal molecular orientation of the cannula material along the desired tear lines.

Hub 70 is located at the proximal end of cannula 60 and is formed with a pair of wings 71 radially extending from a pair of shafts 72. Between each shaft 72 is a groove 72a. Each wing 71 and its associated shaft 72 is aligned on a portion of cannula 60 between each preferential tear line 61 with one of the preferential tear lines 61 located along one groove 72a. This arrangement allows the clinician to pull apart wings 71 and split cannula 60 into two portions along preferential tear lines 61.

Extending between each wing 71 is a tray 75 that extends from the proximal end of cannula 60. In the preferred embodiment, tray has a generally half-cylindrical configuration continuous with a bottom portion of cannula 60. In other words, tray 75 has a semi-circular cross-section with a radius substantially equal to the radius of cannula 60. Importantly, tray 75 has an open top. See FIG. 2a. Although this configuration is preferred, any other configuration for tray 75 could also be used. For example, tray 75 could have a half cone shape, could be flat or could have a flat bottom and parallel sides. All that is required is that tray 75 have an open top and a bottom surface configuration that leads into the open proximal end of cannula 60.

This configuration allows a clinician to automatically align the distal end of a catheter, guidewire or other long, thin and flexible medical device with the open proximal end of cannula 60 for insertion therein by placing the distal end of the medical device onto tray 75. For example, the clinician can lay the distal portion of the catheter or guidewire along the top groove 72a, see FIG. 6, move the catheter or guidewire proximally until the distal end drops on tray 75, and then advance the catheter or guidewire through the open proximal end of introducer 60, see FIGS. 7 and 9. Alternatively, the clinician can drop the distal end of the catheter or guidewire straight down onto tray 75. When the distal end of the catheter or guidewire hits tray 75, the clinician can advance the catheter or guidewire into the open proximal end of introducer 60. See FIG. 8.

Wings 71 are connected to cannula 60 such that the longitudinal axis of cannula 60 extends below the center of mass of wings 71. Preferably the longitudinal axis of cannula 60 is arranged such that about 66% of the center of mass of wings 71 extends above the longitudinal axis of cannula 60. In addition, preferably the longitudinal axis of cannula 60 should be about 0.014 inches below the center of mass of wings 71. As with introducer needle 20 and needle hub 30, this arrangement allows the clinician to approach the venipuncture site with a low insertion angle but still provides sufficient surface area above cannula 60 for a clinician to easily manipulate the device. Moreover, the bottom of wings 71 should not extend significantly below the bottom of tray 75. This also allows the clinician to use a low insertion angle because the bottom of the wings will not be the limiting factor in the insertion angle used. Instead tray 75 becomes the limiting factor.

To use catheter introducer 10, the clinician ensures that it is in the configuration as shown in FIG. 5 with needle bevel 22 facing up and extending distally from the distal end of cannula 60. The clinician approaches the venipuncture site at a low insertion angle and proceeds with the venipuncture. Upon confirmation of blood flashback in the annular space between introducer needle 20 and cannula 60 along the distal portion thereof, the clinician advances cannula 60 further into the vein and removes introducer needle 20. The clinician then places the distal portion of a catheter, guidewire or other long, thin flexible medical device on top of cannula 60 over tray 75. The distal portion is then moved proximally until it drops on tray 75 where it is automatically aligned with the open proximal end of cannula 60. Alternatively, the clinician can drop the distal end of the catheter, guidewire or other long, thin flexible medical device down onto tray 75 where it will be automatically aligned with the open proximal end of cannula 60. The long, thin flexible medical device is then advanced distally into position. At that point, the clinician can manipulate wings 71 to split cannula 60 and remove splittable introducer 50 from the patient. See FIG. 10.

Thus it is seen that a catheter introducer is provided that facilitates aligning the distal end of a long, thin, flexible medical device with the open proximal end of the cannula without having to approach the open proximal end along a line coincident with the longitudinal axis of the cannula and that allows the clinician to use a low insertion angle with the catheter introducer.

We claim:

1. A catheter introducer, comprising:
   an introducer cannula having a proximal portion, an open proximal end, an open distal end, a longitudinal axis and a radius;
   a pair of wings said tray having a semi-circular cross section having a center of mass connected along the proximal portion of the introducer cannula; and
   a tray, with an open top, extending from the open proximal end of the introducer cannula between the pair of wings.

2. The catheter introducer of claim 1 wherein the center of mass of the pair of wings is offset from the longitudinal axis of the introducer cannula.

3. The catheter introducer of claim 2 wherein the center of mass of the pair of wings is above the longitudinal axis of the introducer cannula.

4. The catheter introducer of claim 3 wherein about 66% of the mass of the pair of wings is above the longitudinal axis of the introducer cannula.

5. The catheter introducer of claim 1 wherein the semi-circular cross section has a radius substantially equal to the radius of the introducer cannula.

6. The catheter introducer of claim 1 wherein the introducer cannula includes a pair of longitudinally extending preferential tear lines.

7. The catheter introducer of claim 6 wherein the pair of longitudinally extending preferential tear lines are about 165° apart.

8. A catheter introducer, comprising:
   an introducer cannula having a proximal portion, an open proximal end, an open distal end, a lumen extending between the open proximal end and the open distal end;
   a pair of wings connected along the proximal portion of the introducer cannula;
   a tray, with an open top, extending from the open proximal end of the introducer cannula between the pair of wings said tray having a semi-circular cross section;
   an introducer needle disposed in the lumen of the introducer cannula and defining an annular space with the introducer cannula, the introducer needle having a sharp distal tip, a proximal end, a longitudinal axis and a needle lumen extending between the sharp distal tip and the proximal end; and a needle hub with a center of mass connected to the proximal end of the introducer needle.

9. The catheter introducer of claim 8 wherein the semi-circular cross section has a radius substantially equal to the radius of the introducer cannula.

10. The catheter introducer of claim 8 wherein the introducer needle defines a notch to provide fluid communication between the needle lumen and the annular space.

11. The catheter introducer of claim 8 wherein the center of mass of the needle hub is offset from the longitudinal axis of the needle.

12. The catheter introducer of claim 11 wherein the center of mass of the needle hub is above the longitudinal axis of the needle.

13. A catheter introducer, comprising:

an introducer cannula having a proximal portion, an open proximal end, an open distal end, a lumen extending between the open proximal end and the open distal end, a longitudinal axis and a radius;

a pair of wings having a center of mass connected along the proximal portion of the introducer cannula such that the center of mass is offset from the longitudinal axis of the introducer cannula;

a tray, with an open top, extending from the open proximal end of the introducer cannula between the pair of wings said tray having a semi-circular cross section;

an introducer needle disposed in the lumen of the introducer cannula and defining an annular space with the introducer cannula, the introducer needle having a sharp distal tip, a proximal end, a longitudinal axis and a needle lumen extending between the sharp distal tip and the proximal end; and a needle hub with a center of mass connected to the proximal end of the introducer needle such that the center of mass is offset from the longitudinal axis of the needle.

14. The catheter introducer of claim 13 wherein the semi-circular cross section has a radius substantially equal to the radius of the introducer cannula.

15. The catheter introducer of claim 13 wherein the introducer needle defines a notch to provide fluid communication between the annular space and the needle lumen.

16. The catheter introducer of claim 15 wherein the center of mass of the needle hub is offset from the longitudinal axis of the needle.

17. The catheter introducer of claim 16 wherein the center of mass of the needle hub is above the longitudinal axis of the needle.

18. The catheter introducer of claim 13 wherein the center of mass of the pair of wings is offset from the longitudinal axis of the introducer cannula.

19. The catheter introducer of claim 18 wherein the center of mass of the pair of wings is above the longitudinal axis of the introducer cannula.

20. The catheter introducer of claim 19 wherein about 66% of the mass of the pair of wings is above the longitudinal axis of the introducer cannula.

21. The catheter introducer of claim 13 wherein the introducer cannula includes a pair of longitudinally extending preferential tear lines.

22. The catheter introducer of claim 21 wherein the pair of longitudinally extending preferential tear lines are about 165° apart.

* * * * *